United States Patent [19]

McGee

[11] Patent Number: 5,506,351
[45] Date of Patent: Apr. 9, 1996

[54] PROCESS FOR THE PREPARATION OF 2'-O-ALKYL GUANOSINE AND RELATED COMPOUNDS

[75] Inventor: Daniel P. C. McGee, Carlsbad, Calif.

[73] Assignee: ISIS Pharmaceuticals, Carlsbad, Calif.

[21] Appl. No.: 918,362

[22] Filed: Jul. 23, 1992

[51] Int. Cl.$^6$ .............................. C07H 1/00; C07H 19/167
[52] U.S. Cl. ................. 536/55.3; 536/26.71; 536/26.72; 536/27.81
[58] Field of Search .......................... 536/26.71, 26.72, 536/27.81, 55.3

[56] References Cited

U.S. PATENT DOCUMENTS 5,013,830  5/1991  Ohtsuka et al. ................... 536/25.1

OTHER PUBLICATIONS

Sproat, B. S., Beijer, B. and Iribarren, A., *Nucleic Acids Research*, 18:41–49 (1990).
Robins, M. J., Nairk, S. R. and Lee, A. S. K., *J. Org. Chem.*, 39: 1891–1899 (1974).
Robins, M. J., Hansske, F. and Bernier, S. E., *Can. J. Chem.*, 59: 3360–3364 (1981).
Singer and Kuśmierek, *Biochemistry* 15: 5052–5057 (1976).
Inoue, H., Hayase, Y., Imura, A., Iwai, S., Miura, K. and Ohtsuke, E., *Nucleic Acids Research*, 15: 6131–6148 (1987).
Sproat, B. S., Iribarren, A. M., Garcia, R. G. and Beijer, B., *Nucleic Acids Research*, 19: 733–738 (1991).
B. S. Sproat and A. I. Lamond, "2'-O-Methyloligoribonucleotides: synthesis and applications," *Oligonucleotides and Analogues*, ed. F. Eckstein, (Oxford University Press, 1991): 49–86.
Hansske, F., Madej, D. and Robins, M. J., *Tetrahedron*, 40:125–135 (1984).
Wagner, E., Oberhauser, B., Holzner, A., Brunar, H., Issakides, G., Schaffner, G., Cotten, M., Knollmüller, M. and Noe, C. R., *Nucleic Acids Reasearch*, 19: 5965–5971 (1991).
Gladkaya, V. A., Levitskaya, Z. V., Shalamai, A. S., Usenko, L. S. and Dashevskaya, T. A., *Khim. Prir. Soedin.*, 4: 568 (1989).
Yamauchi, K., Nakagima, T. and Kinoshita, M., *J. Org. Chem.*, 45: 3865–3868 (1980).
Ekborg, G. and Gareg, P. J., *J. Carbohydrates, Nucleosides, Nucleotides*, 7: 57–61 (1980).
Iribarren, A. M., Sproat, B. S., Neuner, P., Sulston, I., Ryder, U. and Lamond, A. I., *Proc. Natl. Acad. Sci.*, 87: 7747–7751 (1990).
Cotten, M., Oberhauser, B., Brunar, H., Holzner, A, Issakides, G., Noe, C. R., Schaffner, G., Wagner, E. and Birnstiel, M. L., *Nucleic Acids Research*, 19: 2629–2635 (1991).
March, *J. Advanced Organic Chemistry*, Wiley–Interscience, John Wiley & Sons, New York, 1985: 220.

*Primary Examiner*—Gary L. Kunz
*Attorney, Agent, or Firm*—Woodcock Washburn Kurtz Mackiewicz & Norris

[57] ABSTRACT

An improved process for preparing 2'-O-substituted guanosine comprising reacting an unprotected 2,6-diaminopurine riboside with an alkyl halide in the presence of a sodium hydride or a base of equal strength followed by a deamination step with adenosine deaminase. Such modified guanosine molecules can be used to synthesize 2'-O-modified oligonucleotides. The above alkylating process can also be used to prepare 3'-O-alkyl- and 2',3'-di-O-alkyl-2,6-diaminopurine ribosides. The deamination of these nucleosides yields the corresponding guanosine derivatives.

13 Claims, No Drawings

PROCESS FOR THE PREPARATION OF 2'-O-ALKYL GUANOSINE AND RELATED COMPOUNDS

CROSS REFERENCE TO RELATED APPLICATIONS

This application is related to application Ser. No. 566,977, "Sugar Modified Oligonucleotides that Detect and Modulate Gene Expression", filed in the U.S. Patent and Trademark Office on Aug. 13, 1990, now abandoned and incorporated by reference herein in its entirety.

FIELD OF THE INVENTION

This invention is directed to improved processes for the preparation of 2'-O-alkyl, 3'-O-alkyl and 2',3'-di-O-alkyl 2,6-diaminopurine riboside, 2'-O-alkyl guanosine and 2'-O-alkyl guanosine analogs and phosphoramidites of these compounds. In the processes of the invention 2,6-diamino-9-(β-D-ribofuranosyl)purine (also identified as 2,6-diaminopurine riboside or 2-aminoadenosine) is alkylated at the 2' and/or 3' positions. The resulting alkylated compounds are then deaminated to the corresponding alkylated guanosine compounds. These in turn can be phosphitylated to phosphoramidite compounds suitable for oligonucleotide synthesis.

BACKGROUND OF THE INVENTION

Antisense therapy involves the use of oligonucleotides having complementary sequences to target RNA or DNA. The antisense oligonucleotide binds to the target RNA or DNA. Upon binding to the target RNA or DNA, the antisense oligonucleotide can selectively inhibit the genetic expression of these nucleic acids or can induce some other events such as destruction of a targeted RNA or DNA or activation of gene expression. Destruction of targeted RNA can be effected by RNase H activation or by linking strand cleavers to the oligonucleotide.

One class of oligonucleotides that have been synthesized are the 2'-O-substituted oligonucleotides. Such oligonucleotides have certain useful properties. In U.S. patent application Ser. No. 814,961, filed Dec. 24, 1991, now abandoned, entitled Gapped 2' Modified Phosphorothioate Oligonucleotides, assigned to the same assignee as this application, the entire contents of which are herein incorporated by reference, 2' substituted nucleotides are introduced within an oligonucleotide to induce increased binding of the oligonucleotide to a complementary target strand while allowing expression of RNase H activity to destroy the targeted strand. In a recent article, Sproat, B. S., Beijer, B. and Iribarren, A., *Nucleic Acids Research*, 18:41 (1990), the authors noted further use of 2'-O-methyl substituted oligonucleotides as "valuable antisense probes for studying pre-mRNA splicing and the structure of spliceosomes".

The advent of automated DNA synthesizers has resulted in ease of synthesis of oligonucleotides having specific sequences of choice. Oligonucleotides are synthesized utilizing nucleotide precursors. These nucleotides, in turn, are synthesized utilizing nucleoside precursors. 2'-O-methyl nucleosides are known; indeed the 2'-O-methyl ether of the four major ribonucleotides occur as minor components in natural RNA. Robins, M. J., Naik, S. R. and Lee, A. S. K., *J. Org. Chem.*, 39:1891 (1974) reported a low yield synthesis of 2'-O- and 3'-O-methyl guanosine via a stannous chloride catalyzed monomethylation by diazomethane. As was later reported by Robins, M. J., Hansske, F. and Bernier, S. E., *Can. J. Chem.*, 59:3360 (1981), "convenient and high yield methods have been devised for synthesis of the 2'-O- and 3'-O-methyl ethers of adenosine, cytidine, and uridine . . . However, guanosine has presented significant difficulties." In the foregoing paper, the authors reported an improved synthesis of 2'-O and 3'-O-methyl guanosine. The synthesis was improved by effecting the stannous chloride catalyzed diazomethane methylation of 2,6-diamino-9-(β-D-ribofuranosyl)purine (2-aminoadenosine) in place of guanosine. The diamino purine moiety was then reduced to the corresponding guanine moiety with adenosine deaminase. In a further diazoation reaction described by Singer and Kusmierek, *Biochemistry* 15: 5052 (1976), a mixture of 2'- and 3'-O-ethyl guanosine was reported to result from the treatment of guanosine with diazoethane. The alkylation also resulted in alkylation of the heterocyclic base. The alkylated product was treated with base to remove the ethyl group from the heterocyclic base. The resulting product was identified by virtue of having the same UV spectrum as that of guanosine, but a Rf differing from the Rf of guanosine.

A further improvement in the synthesis of 2'-O-methyl nucleosides was reported by Inoue, H., Hayase, Y. Imura, A., Iwai, S., Miura, K. and Ohtsuka, E., *Nucleic Acids Research*, 15:6131 (1987). This method of synthesis was effected utilizing $CH_3I$ in the presence of $Ag_2O$. This method proved useful for all of the common nucleotides with the exception of guanosine. As reported by these authors, guanosine proved refractory to this synthetic method. Thus these authors again had to effect the 2'-O-methylation of guanosine with diazomethane. In order to avoid methylation of the amino functionality of the guanine base moiety, the guanine base moiety was blocked with an isobutyryl group. Additionally, to avoid methyl esterification of the 3'-O functionality of the sugar moiety, a TIPDS (tetraisopropyldisiloxane) blocking group was used to block both the 3' and the 5' hydroxyls of the sugar moiety.

The most recent investigators to address the synthesis of 2'-O-methyl guanosine (and 2'-O-allyl guanosine) are Sproat et al., supra and Sproat, B. S., Iribarren, A. M., Garcia, R. G. and Beijer, B., *Nucleic Acids Research*, 19:733 (1991). In both of these Sproat et al. publications, the investigators presented a further synthetic pathway to 2'-O-methylguanosine and 2'-O-allylguanosine. They characterized the further pathway with respect to the prior known synthetic methods as "avoids(ing) . . . the use of the highly toxic and potentially explosive reagent diazomethane" and being "far superior to the use of silver oxide/methyl iodide." This same synthetic method of the Sproat et al. investigators is also published in B. S. Sproat and A. I. Lamond, "2'-O-Methyloligoribonucleotides: synthesis and applications," *Oligonucleotides and Analogues*, ed. F. Eckstein, (IRL Press, 1991). While avoiding the use of diazomethane, when applied to guanosine this latest Sproat et al. synthetic pathway requires six steps to achieve a guanosine compound. Of the six steps in this synthetic pathway, five require separate chromatographic purifications.

A further 2'-O-alkylated guanosine compound is known. This compound, 2'-O-methylthiomethylguanosine, was reported by Hansske, F., Madej, D. and Robins, M. J., *Tetrahedron*, 40:125 (1984). It was produced as a minor by-product of an oxidization step during the conversion of guanosine to 9-β-D-arabinofuranosylguanine, i.e. the arabino analogue of guanosine. The addition of the 2'-O-methylthiomethyl moiety is an artifact from the DMSO solvent utilized during the oxidization procedure. The 2'-O-methylthiomethyl derivative of 2,6-diaminopurine riboside was also reported in the Hansske et al. publication. It was also obtained as an artifact from the DMSO solvent.

It is an object of this invention to provide methods of synthesis of 2'-O-alkylated guanosine and guanosine analogues that avoids the use of diazomethane.

It is a further object of this invention to provide methods of synthesis of 2'-O- and 3'-O-alkylated 2,6-diaminopurine riboside compounds.

It is an additional object of this invention to provide efficient syntheses for 2'-O-alkylated guanosine and guanosine analogs.

BRIEF DESCRIPTION OF THE INVENTION

The present invention provides improved processes for preparing 2'-O-alkyl-guanosine, 2'-O-alkyl guanosine analogs, 2'-O-alkyl-2,6-diaminopurine riboside, 3'-O-alkyl-2,6-diaminopurine riboside, 2',3'-di-O-alkyl-2,6-diaminopurine riboside, the 3'-O-phosphoramidite of 2'-O-alkyl guanosine and the 3'-O-phosphoramidite of 2,6-diamino-9-(2'-O-alkyl-β-D-ribofuranosyl)purine. Additionally the present invention provides improved processes for the preparation of 2,6-diaminopurine riboside.

In accordance with the present invention improved processes for the preparation of 2'-O-alkyl-guanosine and 2'-O-alkyl guanosine analogs comprise treating 2,6-diaminopurine riboside with a base and a compound having the formula R—L wherein R is said alkyl group and L is a leaving group, to form a mixture of 2'-O-alkyl-2,6-diaminopurine riboside and 3'-O-alkyl-2,6-diaminopurine riboside and deaminating the 2'-O-alkyl-2,6-diaminopurine riboside to yield the corresponding 2'-O-alkyl guanosine.

In accordance with the other embodiments of the present invention improved processes for the preparation of 2'-O-alkyl-2,6-diaminopurine riboside, 3'-O-alkyl-2,6-diaminopurine riboside and 2',3'-di-O-alkyl-2,6-diaminopurine riboside comprise treating 2,6-diaminopurine riboside with a base and a compound having the formula R—L wherein R is said alkyl group and L is a leaving group, to format least one of 2'-O-alkyl-2,6-diaminopurine riboside, 3'-O-alkyl-2, 6-diaminopurine riboside or 2',3'-di-O-alkyl-2,6-diaminopurine riboside and isolating one of said 2'-O-alkyl-2,6-diaminopurine riboside, 3'-O-alkyl-2,6-diaminopurine riboside or 2',3'-di-O-alkyl-2,6-diaminopurine riboside.

Processes for the preparation of 3'-O-phosphoramidite of 2'-O-alkyl guanosines include the steps of treating 2,6-diaminopurine riboside with a base and a compound having the formula R—L wherein R is said alkyl group and L is a leaving group, to form 2'-O-alkyl-2,6-diaminopurine riboside; treating said 2'-O-alkyl-2,6-diaminopurine riboside with adenosine deaminase to form 2'-O-alkyl-guanosine; protecting the 2-NH$_2$ moiety of said 2'-O-alkyl-guanosine with a protecting group; protecting the 5'-OH moiety of said 2'-O-alkyl-guanosine with a further protecting group; and phosphitylating the 3'-OH moiety of said protected 2'-O-alkyl-guanosine.

In accordance with the present invention improved processes for preparing the 3'-O-phosphoramidite of 2,6-diamino-9-(2'-O-alkyl-β-D-ribofuranosyl)purine include treating 2,6-diaminopurine riboside with a base and compound having the formula R—L wherein R is said alkyl group and L is a leaving group, to form 2'-O-alkyl-2,6-diaminopurine riboside; protecting the 2 and 6 —NH$_2$ moieties of said 2,6-diamino-9-(2'-O-alkyl-β-D-ribofuranosyl)purine with protecting groups; protecting the 5'-OH moiety of said 2,6-diamino-9-(2'-O-alkyl-β-D-ribofuranosyl)purine with a further protecting group; and phosphitylating the 3'-OH moiety of said protected 2,6-diamino-9-(2'-O-alkyl-β-D-ribofuranosyl)purine.

Also in accordance with the present invention an improved processes for the preparation of 2,6-diaminopurine riboside includes treating guanosine hydrate with hexamethyldisilazane and trifluoromethane sulfonic acid in a sealed container with the exclusion of liquid ammonia and under non-anhydrous conditions and isolating the product such as by crystallization.

DETAILED DESCRIPTION OF THE INVENTION

For the purposes of this invention the terms "alkyl", "alkylation", "alkylated" and the like are defined to include the alkanes, the alkenes, the alkynes and their corresponding alicyclic analogues but excluding aromatic compounds. These terms thus include the aliphatic and alicyclic members of the hydrocarbons.

This invention includes processes for the facile preparation of 2'-O and 3'-O-monoalkyl or 2',3'-di-O-alkyl substituted guanosine compounds. Except for preparation with diazomethane, heretofore, direct alkylation of guanosine has proven to be refractory. The present invention provides direct 2' and 3' -O-alkylation of 2,6-diamino-9-(-β-D-ribofuranosyl)purine, i.e. 2,6-diaminopurine riboside or 2-aminoadenosine, which can be effected followed by deamination of the 2'-O-alkylated 2,6-diamino purine riboside to the corresponding 2'-O-alkylated guanosine. This alkylation can be practiced, if desired, without the use of blocking groups on either the heterocycle or the sugar moieties of the nucleoside. Further unlike the use of diazomethane, which will only yield the methyl alkylation product, alkylation as practiced in this invention is not limited to just methyl alkylation but is used to yield a plenitude of alkyl substituted guanosine and 2,4-diaminopurine riboside compounds. The necessary compounds used in the invention having the formula R—L wherein R is an alkyl group and L is a leaving group, are either commercially available, are known in the literature or can be prepared by procedures analogous to known literature compounds.

The two step alkylation processes of the invention are further distinguished from the six step procedure of the Sproat et al. investigators. See the above-referenced *Nucleic Acids Research*, 18:41 (1990) and *Nucleic Acids Research*, 19:733 (1991) publications. In those procedures 2-amino-6-chloropurine riboside must first be blocked at both the 3' and 5' positions, converted to the 2,6-dichloro derivative, blocked at the 6 purine position, derivatized to the 2'-O-methyl or 2'-O-allyl derivative, converted to 2,6-diamino derivative, deblocked about the 3' and 5' positions and finally deaminated to the 2'-O-methyl or 2'-O-allyl guanosine product.

In accordance with the processes of this invention, alkylation is effected directly on 2,6-diamino-9-(β-D-ribofuranosyl)purine with an appropriate compound having the formula R—L, wherein R is an alkyl group and L is a leaving group, in the presence of a base of sufficient strength to effect removal of the proton from the 2' or 3' (or both 2' and 3') hydroxyl of the ribofuranosyl sugar moiety of 2,6-diamino-9-(β-D-ribofuranosyl)purine. Alkylation can be limited to mono alkylation by limiting the amount of either the R—L group or the base to a stoichiometric (or equivalent) amount. Alternately dialkylation (on both the 2' and 3' positions) can be practiced by use of an excess R—L group and base to concurrently alkylate both the 2' and the 3' positions.

While not wishing to be bound by theory, it has been observed that alkylation predominates at the 2' position compared to the 3' position. Generally a ratio of from about 7:3 to about 8:2 of 2' to 3' alkylation products are obtained (as determined by TLC). For both TLC as well as preparative scale chromatography, the 2' product generally has a faster Rf than the 3' product. Advantage can be taken of this Rf difference to separate the 2'-O- and 3'-O- products from each other or from 2'-O-,3'-O- dialkylated products. Thus the 2' and 3' alkylation products can be separated by procedures such as silica gel chromatography if desired. For alkyl groups that are generally larger than propyl, further advantage can be taken of the rate of deamination of the 2' product verse the 3' product for separation of the 2'-O and 3'-O products. Thus mixtures of 2'-O and 3'-O alkylated 2,6-diamino-9-(β-D-ribofuranosyl)purine are subjected to deamination with adenosine deaminase. The enzymatic deamination of the 2'-O product is more facile than deamination of the 3'-O product. This difference in the rate of deamination allows for separation of the deaminated 2' product, i.e. the 2'-O-alkylated guanosine, from the slower or non-deaminated 3' product, i.e. the 2,6-diamino-9-(3'-O-alkylated-β-D-ribofuranosyl)purine. Additionally procedures such as crystallization has been utilized to further separate a 2' product from the corresponding 3' product by separating the 2'-O-alkylated diaminopurine riboside product from the corresponding 3'-O-alkylated diaminopurine riboside product.

A preferred base utilized for alkylation is sodium hydride. Other suitable bases may also be utilized, however such bases must have sufficient base strength to remove the proton from the 2' (or 3') hydroxyl moiety of the 2,6-diaminopurine riboside starting material. While not wishing to be bound by theory, generally any base having a $pK_a$ about 10 $pk_a$ units greater than the $pK_a$ of the proton of the 2' hydroxyl moiety of the 2,6-diaminopurine riboside starting material may be used. More specifically, bases having a $pK_b$ greater than the $pK_b$ of sodium hydride may conveniently be selected. Such bases can be selected from compilations of base such as those given in Table 1, page 220 of March, *J. Advanced Organic Chemistry*, Wiley-Interscience, John Wiley & Sons, New York, 1985.

The alkylation reactions of the invention typically are conducted in DMF as the solvent. Other suitable solvents include DMSO, N-methyl pyrolidone and sulfolone.

Preferably, deamination is effected by use of deaminase enzymes. Particularly preferred is adenosine deaminase. Particularly suitable for use is Adenosine Deaminase Type II available from Sigma Chemical Company, St. Louis, Mo. Other deamination reagents may also be employed. The deamination reactions of the invention typically are conducted in a mixture solvent containing an organic solvent and an aqueous buffer. Suitable for use as the organic solvent are DMSO, N-methyl pyrolidone and sulfolone. In preferred embodiments of the present invention deamination is achieved using DMSO as the organic solvent. Suitable for use as the aqueous buffer are buffers having a pH compatible to the pH range of use of the deaminase enzyme. Preferred are phophate buffers such as sodium phosphate and tris buffers.

In order to enrich the 2' product verse 3' product by elimination of any 3' product, a TIPDS (tetraisopropylsiloxane) protecting group is utilized to protect the 3' and 5' hydroxyl moieties of the sugar portions of the 2,6-diaminopurine riboside. In the same manner, exclusive 3' product would be obtainable by use of a base stable, non-migratory 2'-O-protecting group. Such base stable, non-migratory protecting groups include but are not limited to tetrahydropyranyl (THP), 4-methoxytetrahydropyran-4-yl (Mthp), 1-[(2-chloro-4-methyl)phenyl-4-methoxypiperidin-4-yl (Ctmp), triphenylmethyl (trityl), mono-, di- and tri-methoxytrityl and other similar protecting groups.

Aliphatic and alicyclic groups suitable for use in the invention include but are not limited to saturated and unsaturated, straight and branch chain and alicyclic, substituted and unsubstituted alkyl, alkenyl and alkynyl groups including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon straight-chain alkyl groups; 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched-chain groups; allyl, crotyl, propargyl, 2-pentenyl and other unsaturated groups; and cyclohexane, cyclopentane, adamantane as well as other alicyclic groups. Preferred compounds are the $C_1$–$C_{20}$ alkyls, $C_1$–$C_{20}$ alkenes and $C_1$–$C_{20}$ alkynes. Most preferred are the $C_1$–$C_{20}$ straight chain alkyls.

Further included are aliphatic and alicyclic groups (as defined above) that include substituent groups thereon. Such substituent groups include but are not necessarily limited to halogen (Cl, Br, F), hydroxyl (OH), thiol (SH), keto (C=O), carboxyl (COOH), nitrate ($ONO_2$), nitro ($NO_2$), nitroso (NO), nitrile (CN), trifluoromethyl ($CF_3$), trifluoromethoxy ($OCF_3$), O-alkyl, S-alkyl, NH-alkyl, N-dialkyl, O-aralkyl, S-aralkyl, NH-aralkyl, amino ($NH_2$), azido ($N_3$), hydrazino ($NHNH_2$), hydroxylamino ($ONH_2$), isocyanato (OCN), sulfoxide (SO), sulfone ($SO_2$), sulfide (S—), disulfide (S—S), silyl, heterocyclic, alicyclic, carbocyclic, intercalators, reporter molecules, conjugates, polyamines, polyamides, polyethylene glycols, polyethers, groups that enhance the pharmacodynamic properties of oligonucleotides, and groups that enhance the pharmacokinetic properties of oligonucleotides. Such compounds include 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups. These substituted groups can be introduced in a blocked or protected form and later de-blocked to the parent substituted compound. For example, use of the phthalimido group as a blocked form of an amino substitution is illustrated below.

One particularly preferred substituent group is $CF_3$. Further particularly preferred substituent groups are phthalimido and imidazole. As noted, use of the phthalimido group allows for introduction of a blocked amino functionality on the alkyl group. Utilizing guanosine analogues prepared in accordance with this invention as intermediates in oligonucleotide synthesis, after oligonucleotide synthesis is complete, the phthalimido group is removed yielding an amino functionality tethered to a guanosine nucleotide within the oligonucleotide sequence. Use of an imidazole moiety as a substituent group on the alkyl functionality introduces the suggested nucleic acid cleaving functionality, imidazole, on a guanosine nucleotide within an oligonucleotide sequence.

Typical intercalators, reporter molecules and conjugates include cholesterols, phospholipids, biotin, phenanthroline, phenazine, phenanthridine, anthraquinone, acridine, fluoresceins, rhodamines, coumarins, and dyes. Halogens include fluorine, chlorine, bromine, and iodine. Groups that enhance the pharmacodynamic properties, in the context of this invention, include groups that improve oligonucleotide uptake, enhance oligonucleotide resistance to degradation, and/or strengthen sequence-specific hybridization with RNA. Groups that enhance the pharmacokinetic properties, in the context of this invention, include groups that improve oligonucleotide uptake, distribution, metabolism or excretion.

Suitable leaving groups of the present invention include halides such as chloride, bromide, and iodide, sulfonates such as tosyl, brosyl, nosyl, mesyl and trifyl and oxonium ions. In preferred embodiments of the present invention the leaving group is a halide. Still other suitable leaving groups are well known to those skilled in the art.

The 3'-O-phosphoramidite of 2'-O-alkyl guanosine and 2,6-diamino-9-(2'-O-alkyl-β-D-ribofuranosyl) purine can be provided in some embodiments of the present invention by reaction of 2-$NH_2$, 5'-OH protected 2'-O-alkyl guanosine or 2-$NH_2$, 6-$NH_2$, and 5'-OH protected 2,6-diamino-9-(2'-O-alkyl-β-D-ribofuranosyl) purine with commercially available reagent known to those skilled in the art such as 2-cyanoethyl N,N-diisopropylaminochlorophosphine.

2'-O-alkyl guanosine and 2'-O-alkyl-2,6-diaminopurine riboside may be phosphitylated at the 3'-OH to provide phosphoramidites by methods known in the art such as by protection of the $NH_2$ moieties (2- or 2- and 6- $NH_2$, respectively) and 5'-OH moiety followed by reaction with cyanoethyl N,N-diisopropyl aminochlorophosphine.

EXAMPLES

The following examples illustrate the invention, however, they are not intended as being limiting.

EXAMPLE 1

2,6-Diamino-9-(β-D-ribofuranosyl)purine

In accordance with modifications of the procedures described in Robins, M. J., Hanske, F. and Beriner, *S. E., Can. J. Chem.*, 59:3360 (1981), guanosine hydrate (49 g, Aldrich Chemical Co.), toluene (200 ml), hexamethyldisilazane (160 ml, 4.3 eq) and trifluoromethanesulfonic acid (3.7 ml) were loaded in a stainless steel Parr bomb. The bomb was sealed and heated approximately ⅓ submerged in an oil bath at 170° C. for 5 days. The bomb was cooled in a dry ice acetone bath and opened. The contents were transferred to a 2 liter round bottom flask using methanol (MeOH) and the solvent evaporated on a Buchii evaporator. 1:1 $H_2O$/MeOH (600 ml) was added to the residue and the resulting brown suspension was refluxed 4–5 hr. The resulting suspension was evaporated on the Buchii evaporator to remove the methanol (≈½ volume). Additional $H_2O$ (≈300 ml) was added and the mixture was heated, treated with charcoal and filtered through a Celite filter pad. Upon cooling, a crystalline solid formed. The solid was isolated by filtration, washed with $H_2O$ and dried under high vacuum at 90° C. to yield the product (43.7 g, 89% yield) as a tan solid. UV and NMR spectra of this compound compared to literature values.

This variation of the procedures of Robins, et al. supra, eliminated the need to utilize liquid ammonia in the reaction mixture since the ammonia molecule is generate in situ from the silazane reagent and the water of hydration of the guanosinehydrate starting material. Further, the use of chlorotrimethylsilane was not necessary nor was it necessary to conduct the reaction under anhydrous conditions, to do a preliminary evaporation, or to open and re-seal the Parr bomb under a dry nitrogen atmosphere.

EXAMPLE 2

2,6-Diamino-9-(2-O-propyl-β-D-ribofuranosyl)purine & 2,6 -Diamino-9-(3-O-propyl-β-D-ribofuranosyl)purine Sodium hydride (NaH) (2.1 g) was added to 2,6-diamino-9-(β-D-ribofuranosyl) purine (10.5 g) in dry dimethylformamide (DMF) (150 ml). After stirring for 10 min, iodopropane (6 ml) was added. The solution was stirred for 45 min at room temperature followed by the addition of a further aliquot of NaH (600 mg). The reaction mixture was stirred overnight and then quenched by the addition of ethanol (EtOH) (5 ml). The reaction mixture was evaporated in vacuo, the residue suspended in 10% MeOH/$CH_2CL_2$ and purified by silica gel chromatography (300 g) using 5→10% MeOH/$CH_2Cl_2$ as the eluent. The 2',3'-di-O-propyl product eluted first followed by the 2'-O-propyl product and then the 3'-O-propyl product. The 2'-O-propyl product containing fractions were pooled and the solvent stripped to yield a crude foam. The foam was crystallized from $H_2O$ (40 ml), washed with cold $H_2O$ and dried to yield 2.9 g of the 2'-O-propyl compound. The mother liquor was evaporated, re-chromatographed and crystallized to yield an additional 2.4 g of the 2'-O-propyl compound. The second mother liquor was evaporated to yield 4 g of a mixture of 2' and 3'-O-propyl compounds as an oil. Fractions containing the 3'-O-propyl product as the major product were evaporated and residue foam crystallized from water. (See Example 17 below for isolation and characterization of the 2',3'-di-O-propyl compound).

2,6-Diamino-9-(2-O-propyl-β-D-ribofuranosyl)purine $^1$H NMR (DMSO-$d_6$) δ 0.76 (t, 3, C$\underline{H}_3$), 1.4 (tq, 2, C$\underline{H}_2$), 3.3 (m, 1, $\underline{H}$-5"+HDO), 3.65–3.45 (m, 3, $\underline{H}$-5', O—C$\underline{H}_2$), 3.9 (m, 1), 4.25 (br m, 1), 4.38 (dd, 1), 5.1 (br d, 1 3'-O$\underline{H}$), 5.45 (br t, 1, 5'-OH), 5.75 (br s, 2, 6-N$\underline{H}_2$), 5.83 (d, 1, $\underline{H}$-1'), 6.77 (br s, 2, 2-N$\underline{H}_2$) and 7.95 (s, 1, $\underline{H}$-8). Anal. Calcd. for $C_{13}H_{20}N_6O_4$·½$H_2O$: C, 46.91; H, 6.2; N,25.25. Found: C, 47.09; H, 6.37; N, 25.33.

2,6-Diamino-9-(3-O-propyl-β-D-ribofuranosyl)purine $^1$H NMR (DMSO-$d_6$) δ 0.75 (t, 3, C$\underline{H}_3$), 1.4 (tq, 2, C$\underline{H}_2$), 3.27–3.5 (ABX 2, O—C$\underline{H}_2$—), 3.5 and 3.6 (ABX, 2, $\underline{H}$-5'), 3.9 (m, 1), 4.22 (m, 1), 4.35 (m, 1), 5.1 (br d, 1, 2'-O$\underline{H}$), 5.45 (br t, 1, 5'-O$\underline{H}$), 5.75 (br s, 2, 6-N$\underline{H}_2$), 5.8 (d, 1, $\underline{H}$-1'), 6.8 (br s, 2, 2 -$\underline{H}_2$) and 7.95 (s, 1, $\underline{H}$-8).

EXAMPLE 3

2'-O-Propylguanosine

A mixture of 2,6-Diamino-9-(2'-O-propyl-β-D-ribofuranosyl) purine and 2,6-Diamino-9-(3'-O-propyl-β-D-ribofuranosyl) purine (4.6 gm) and adenosine deaminase (200 mg, Sigma Chemicals Type II) were stirred at room temperature overnight in 0.1M tris buffer (150 ml, pH 7.4), DMSO (100 ml) and 0.1M sodium phosphate buffer (10 ml). A further aliquot of adenosine deaminase (140 mg) in 0.1M phosphate buffer (30 ml) and DMSO (20 ml) was added and the reaction stirred an addition 24 hrs. The solvent was evaporated in vacuo and the residue flash chromatographed on silica gel utilizing 5→20% MeOH/$CH_2Cl_2$. Product-containing fractions were evaporated in vacuo and the residue crystallized from $H_2O$ to yield 2.6 gm of product. m.p. dec>270° C. $^1$H NMR (DMSO-$d_6$) δ 0.75 ( t, 3, C$\underline{H}_3$), 1.42 (tq, 2, C$\underline{H}_2$ ), 3.3–3.6 (m, 4, $\underline{H}$-5', O—C$\underline{H}_2$), 3,85

(m, 1), 4.2 (m, 1), 4.23 (m, 1), 5.10 (t, 1, 5'-O$\underline{H}$), 5.13 (d, 1, 3'-O$\underline{H}$), 5.75 (d, 1, $\underline{H}$-1'), 6.45 (br s, 2, N$\underline{H}_2$), 7.95 (s, 1, $\underline{H}$-8) and 10.67 (br s, 1, N$\underline{H}$). Anal. Calcd. for $C_{13}H_{19}N_5O_5$: C, 47.99; H, 5.89; N, 21.53. Found: C, 47.90, H, 5.85; N, 21.44.

EXAMPLE 4

N2-Isobutyryl-2'-O-propylguanosine

2'-O-Propylguanosine (3.6 gm) in pyridine (50 ml) was cooled in an ice bath and trimethylsilyl chloride (8.4 ml, 6 eq.) was added. The reaction mixture was stirred for 30 min and isobutyryl chloride (5.8 ml, 5 eq.) was added. The solution was stirred for 4 hours during which it was allowed to warm to room temperature. The solution was cooled, $H_2O$ added (10 ml) and the solution was stirred for an additional 30 mins. Concentrated $NH_4OH$ (10 ml) was added and the solution evaporated in vacuo. The residue was purified by silica gel chromatography using 10% MeOH/$CH_2CL_2$ to elute the product. Product-containing fractions were evaporated to yield 2.5 g of product as a foam. An analytical sample was re-chromatographed on silica and eluted with $CH_2Cl_2 \rightarrow 6\%$ MeOH/$CH_2Cl_2$. $^1$H NMR (DMSO-$d_6$) δ 0.75 (t 3, C$\underline{H}_3$) 1.13 [d, 6, CH(C$\underline{H}_3$)$_2$], 1.4 (m, 2, C$\underline{H}_2$), 2.75 [m, 1, C$\underline{H}$(CH$_3$)$_2$], 3.52 (m, 6, OC$\underline{H}_2$), 3.36 and 3.6 (ABX, 2, $\underline{H}$-5'), 3.95 (m, 1), 4.26 (m, 1), 4.33 (m, 1), 5.07 (t, 1, 5'-O$\underline{H}$), 5.18 (d, 1, 3'-O$\underline{H}$), 5.9 (d, 1, $\underline{H}$-1'), 8.25 (s, 1, $\underline{H}$-8), 11.65 (br s, 1, N$\underline{H}$) and 12.1 (br s, 1, N$\underline{H}$). Anal. Calcd. for $C_{17}H_{25}N_5O_6.\frac{1}{2}H_2O$: C, 50.49; H, 6.48; N, 17.32. Found: C, 50.81; H, 6.62; N, 17.04.

EXAMPLE 5

N2-Isobutyryl-5'-dimethoxytrityl-2'-O-propylguanosine

N2-Isobutyryl-2'-O-propylguanosine (2.64 g) was co-evaporated with pyridine and then solubilized in pyridine (180 ml). Dimethoxytrityl chloride (2.4 g, 1.1 eq) and dimethylaminopyridine (50 mg) was added with stirring at room temperature. The reaction mixture was stirred overnight and evaporated in vacuo. The residue was partitioned between $CH_2Cl_2/2\times$dil $Na_2CO_3$. The organic phase was dried (MgSO$_4$) and evaporated. The residue was purified by silica gel chromatography (1:1 EtOAc/Hex$\rightarrow$5% MeOH/EtOAc, 1% TEA) to yield 4.1 g of product. $^1$H NMR (DMSO-$d_6$) δ 0.78 (t, 3, C$\underline{H}_3$), 1.12 [d, 6, CH(C$\underline{H}_3$)$_2$], 1.46 (m, 2, C$\underline{H}_2$), 2.75 [m, 1, C$\underline{H}$(CH$_3$)$_2$], 3.35 and 3.55 (ABX, 2, $\underline{H}$-5'), 3.73 (s, 6, OC$\underline{H}_2$), 4.0 (m, 1), 4.3 (m, 1), 4.4 (m, 1), 5.18 (d, 1, 3'-O$\underline{H}$), 5.93 (d, 1, $\underline{H}$-1'), 6.8, 7.2, 7.36 (m, 13, DMTr), 8.13 (s, 1, $\underline{H}$-8), 11.63 (br s, 1, N$\underline{H}$) and 12.1 (br s, 1, N$\underline{H}$). Anal. Calcd. for $C_{38}H_{42}N_5O_8.H_2O$: C, 63.83; H, 6.20; N, 9.80. Found: C, 64.22; H, 6.35; N, 9.55.

EXAMPLE 6

N2-Isobutyryl-5'-dimethoxytrityl-2'-O-propylguanosine 3'-β-cyanoethyl-N,N-diisopropylphosphoramidate A $CH_2Cl_2$ solution of N2-Isobutyryl-5'-dimethoxytrityl-2'-O-propylguanosine (4.1 g), bis-(N,N-diisopropylamino)-2-cyanoethylphosphite (3.7 ml, 2 eq) and N,N-diisopropylammoniumtetrazolide (0.5 g, 0.5 eq) was stirred at room temperature overnight. The solution was partitioned against dil. $Na_2CO_3$ and then dil. $Na_2CO_3$/NaCl and dried over MgSO$_4$. The solvent was evaporated in vacuo and the residue was purified by silica gel chromatograph (120 g, 1% TEA in EtOAc) to yield 5.2 g of product as a foam. $^{31}$P NMR (CDCl$_3$) δ 150.5, 150.8.

EXAMPLE 7

2,6-Diamino-9-(2-O-pentyl-β-D-ribofuranosyl)purine & 2,6-Diamino-9-(3-O-pentyl-β-D-ribofuranosyl)purine 2,6-Diamino-9-(β-D-ribofuranosyl)purine (10 g) was treated with sodium hydride (1.7 g, 1.2 eq) and bromopentane (5.3 ml, 1.2 eq) in DMF (90 ml) as per the procedure of Example 2. Silica gel chromatography yielded three components. The first eluted component (not characterized but believed to be the 2,3-di-(O-pentyl) compound was isolated as an oil (700 mg). The next component isolated as a foam (3.3 g) was crystallized from MeOH to yield of 2.8 g of 2,6-diamino-9-(2-O-pentyl-β-D-ribofuranosyl)purine. The third component isolated as a solid (200 mg) was crystallized from MeOH to yield 80 mg of 2,6-diamino-9-(3-O-pentyl-β-D-ribofuranosyl)purine. Fractions containing mixtures of the first and second components were evaporated and the residue crystallized from MeOH to yield a further 900 mg of the 2-O-pentyl compound. Further fraction yielded 1.2 g of a mixture of the 2'-O-pentyl and 3'-O-pentyl compounds.

2,6-Diamino-9-(2-O-pentyl-β-D-ribofuranosyl)purine $^1$H NMR (DMSO-$d_6$) δ 0.75 (t, 3, C$\underline{H}_3$), 1.16 (m, 4, C$\underline{H}_2$), 1.39 (m, 2, C$\underline{H}_2$), 3.53 (m, 2, C$\underline{H}_2$), 3.3 and 3.6 (ABX, 2, $\underline{H}$-5'), 3.93 (br s, 1), 4.23 (m, 1), 4.38 (m, 1), 5.1 (d, 1 3'-O$\underline{H}$), 5.5 (t, 1, 5'-OH), 5.75 (br s, 2, 6-N$\underline{H}_2$), 5.82 (d, 1, $\underline{H}$-1'), 6.8 (br s, 2, 2-N$\underline{H}_2$) and 7.93 (s, 1, $\underline{H}$-8).

2,6-Diamino-9-(3-O-pentyl-β-D-ribofuranosyl)purine $^1$H NMR (DMSO-$d_6$) δ 0.87 (t, 3, C$\underline{H}_3$), 1.3 (m, 4, C$\underline{H}_2$), 1.55 (m, 2, C$\underline{H}_2$), 3.5 (m, 2, O—C$\underline{H}_2$—), 3.6 (m, 2, $\underline{H}$-5'), 3.86 (m, 1), 3.95 (m, 1), 4.6 (m, 1), 5.32 (br d, 1 2'-O$\underline{H}$), 5.46 (br t, 1, 5'-OH), 5.70 (d, 1, $\underline{H}$-1'), 5.75 (br s, 2, 6-N$\underline{H}_2$), 6.76 (br s, 2, 2-N$\underline{H}_2$) and 7.93 (s, 1, $\underline{H}$-8).

EXAMPLE 8

2'-O-Pentylguanosine 2,6-diamino-9-(2-O-pentyl-β-D-ribofuranosyl)purine (1.9 g) in 0.1M sodium phosphate buffer (50 ml, pH 6.0) and DMSO (25 ml) was treated with adenosine deaminase (added in two aliquots—first aliquot 50 mg, second aliquot 80 mg) at 35° C. as per the procedure of Example 3 to yield 1.4 g of product. $^1$H NMR (DMSO-$d_6$) δ 0.8 (t, 3, C$\underline{H}_3$), 1.16 (m, 4, 2×C$\underline{H}_2$), 1.4 (m, 2, C$\underline{H}_2$), 3.38, 3.6 (m, 4, OC$\underline{H}_2$, $\underline{H}$-5'), 3.93 (s, 1, $\underline{H}$-4'), 4.28 (m, 2, $\underline{H}$-2', $\underline{H}$-3'), 5.17 (br, 2, 5', 3'-O$\underline{H}$), 5.8 (d, 1, $\underline{H}$-1'), 6.53 (br s, 2, N$\underline{H}_2$), 8.0 (s, 1, $\underline{H}$-8) and 10.68 (br, 1, N$\underline{H}$).

EXAMPLE 9

N2-Isobutyryl-2'-O-pentylguanosine

2'-O-pentylguanosine (2.3 g) in pyridine (35 ml) was treated with trimethylsilyl chloride (4.15 ml, 5 eq) and isobutyryl chloride (3.4 ml, 5 eq) as per the procedure of Example 4 to yield the product as a foam (2.3 g). An analytical sample was crystallized from EtOAc/Hex. m.p. 178°–180° C. $^1$H NMR (DMSO-$d_6$) δ 0.75 (t, 3, C$\underline{H}_3$), 1.1 [m, 10, 2×C$\underline{H}_2$, CH(C$\underline{H}_3$)$_2$], 1.4 (m, 2, C$\underline{H}_2$), 2.74 [m, 1, C H(CH₃)₂], 3.56 (m, 4, OC$\underline{H}_2$, $\underline{H}$-5), 3.93 (m, 1, H-4'), 4.25 (m, 1), 4.34 (m, 1), 5.05 (t, 1, 5'-O$\underline{H}$), 5.17 (d, 1, 3'-O$\underline{H}$), 5.88 (d, 1, $\underline{H}$-1'), 8.27 (s, 1, $\underline{H}$-8), 11.65 (br s, 1, N$\underline{H}$) and 12.05 (br s, 1, N$\underline{H}$). Anal. Calcd. for C₁₉H₂₉N₅O₆: C, 53.89; H, 6.90; N, 16.54. Found: 53.75; H, 6.92; N, 16.40

EXAMPLE 10

N2-Isobutyryl-5'-dimethoxytrityl-2'-O-pentylguanosine

N2-Isobutyryl-2'-O-pentylguanosine (2.3 g) was treated with dimethoxytrityl chloride (1.7 g, 1.1 eq), and dimethylaminopyridine (100 mg as a catalyst) in pyridine (50 ml) as per the procedure of Example 5 to yield the product as a foam (2.9 g). ¹H NMR (DMSO-$\underline{d}_6$) δ 0.83 (t, 3, C$\underline{H}_3$), 1.2 [m, 10, 2×C$\underline{H}_2$, CH(C$\underline{H}_3$)₂], 1.48 (m, 2, C$\underline{H}_2$), 2.78 [m, 1, C$\underline{H}$(CH₃)₂], 3.4, 3.6 (m, 4, OC$\underline{H}_2$, $\underline{H}$-5'), 3.75 (s, 6, OC$\underline{H}_3$), 4.07 (m, 1), 4.27 (m, 1), 4.42 (m, 1), 5.2 (br d, 1, 3'-O$\underline{H}$), 5.95 (d, 1, $\underline{H}$-1'), 6.85, 7.25, 7.38 (m, 13, DMTr), 8.15 (s, 1, $\underline{H}$-8), 11.67 (br s, 1, N$\underline{H}$) and 12.1 (br s, 1, N$\underline{H}$). Anal. Calcd. for Anal. Calcd. for C₄₀H₄₇N₅O₈·½H₂O: C, 65.38; H, 6.58; N, 9.53. Found: C, 65.37; H, 6.59; N, 9.39.

EXAMPLE 11

N2-Isobutyryl-5'-dimethoxytrityl-2'-O-pentylguanosine 3'-β-cyanoethyl-N,N-diisopropylphosphoramidate N2-Isobutyryl-5'-dimethoxytrityl-2'-O-pentylguanosine (1.7 g) was treated with bis-(N,N-diisopropylamino)-2-cyanoethyl-phosphite (1.48 g) and N,N-diisopropylammonium tetrazolide (200 mg) as per the procedure of Example 6 to yield the product (1.4 g). ³¹P NMR (CDCl₃) δ 150.5, 150.85.

EXAMPLE 12

2,6-Diamino-9-(2-O-nonyl-β-D-ribofuranosyl)purine 2,6-Diamino-9-(β-D-ribofuranosyl)purine (50 g, 180 mmol) was treated with sodium hydride (8.8 g, 220 mmol) and bromononane (59 g, 54.4 ml, 285 mmol) in DMF (700 ml) as per the procedure of Example 2 (the diamino compound in DMF was cooled in an ice bath during the addition of NaH) to yield 83 g of crude product. 50 g of crude product was purified by silica gel chromatography. Fraction containing 2'-O-nonyl and 3'-O-nonyl product were combined to give a 77:23 mixture (29 g) of the 2' and 3' product. Pure 2'-O-nonyl product is obtained by chromatography. ¹H NMR (DMSO-$\underline{d}_6$) δ 0.95 (t, 3, C$\underline{H}_3$); 1.17 [m, 12, O—CH₂—CH₂—(C$\underline{H}_2$)₆ ]; 1.42 [m, 2, O—CH₂C$\underline{H}_2$(CH₂)₆]; 3.27–3.70 (m, 2, $\underline{H}$-5'); 3.50–3.70 [m, 2, O—C$\underline{H}_2$(CH₂)₇]; 3.95 (m, 1, H-4'), 4.24 (m, 1, $\underline{H}$-3'); 4.40 (m, 1, $\underline{H}$-2'); 5.10 (d, 1, 3'-O$\underline{H}$, J=5 Hz); 5.50 (t, 1, 5'-O$\underline{H}$, J=6 Hz); 5.76 (s, 2, 2-N$\underline{H}_2$); 5.83 (d, 1, $\underline{H}$-1', J=6.0 Hz); 6.81 (s, 2, 6-N$\underline{H}_2$); and 7.96 (s, 1, 8-$\underline{H}$).

EXAMPLE 13

2'-O-Nonylguanosine

A mixture of 2,6-diamino-9-(2-O-nonyl-β-D-ribofuranosyl)purine and 2,6-diamino-9-(3-O-nonyl-β-D-ribofuranosyl)purine (≈80:20 mixture, 29 g) in 0.1M sodium phosphate buffer (50 ml, pH 7.4), 0.1M tris buffer (1800 ml, pH 7.4) and DMSO (1080 ml) was treated with adenosine deaminase (1.6 g) as per the procedure of Example 3 to yield 60 g of product as an oil. An analytical product was purified by silica gel chromatography and recrystallized from EtOAc. m.p. 258°–259° C. ¹H NMR (DMSO-$\underline{d}_6$) δ 0.96 (t, 3, C$\underline{H}_3$, J= 7 Hz); 1.17 [m, 12, O—CH₂—CH₂—(C$\underline{H}_2$)₆]; 1.42 [m, 2, O—CH₂C$\underline{H}_2$(CH₂)₆]; 3.27–3.61 (m, 4, $\underline{H}$-5', O—C$\underline{H}_2$(CH₂)₇]; 3.95 (m, 1, $\underline{H}$- 4'), 4.10–4.13 (m, 2, $\underline{H}$-2', $\underline{H}$-3'); 5.13–6.06 (m, 2, 3'-O$\underline{H}$, 5'-O$\underline{H}$); 5.80 (d, 1, $\underline{H}$-1', J=6.4 Hz); 6.47 (s, 2, 2-N$\underline{H}_2$); 7.98 (s, 1, 8-$\underline{H}$) and 10.64 (s, 1, N₁ amide). Anal. Calcd. for C₁₉H₃₁N₅O₅: C, 55.73; H, 7.63; N, 17.10. Found: C, 55.67; H, 7.66; N, 17.02.

EXAMPLE 14

N2-Isobutyryl-2'-O-nonylguanosine

2'-O-nonylguanosine (14.7 g) in pyridine (360 ml) was treated with trimethylsilyl chloride (23.4 ml) and isobutyryl chloride (30.6 ml) as per the procedure of Example 4 to yield crude product (37 g). The crude material was purified by silica gel chromatography (eluted with 90/10 CHCl₃/MeOH) to yield 14.6 g of product re-crystallized from EtOAc. m.p. 168°–169° C. ¹H NMR (DMSO-$\underline{d}_6$) δ 0.85 [t, 3, C$\underline{H}_3$(nonyl)], 1.14 [m, 18, O—CH₂CH₂(C$\underline{H}_2$)₆ , CH(C$\underline{H}_3$)₂], 1.40 [m, 2, O—CH₂C$\underline{H}_2$(CH₂)₆], 2.79 [m, 1, C$\underline{H}$(CH₃)₂], 3.31–3.63 (m, 4, $\underline{H}$-5', O—C$\underline{H}_2$(CH₂)₇]; 3.96 (m, 1, $\underline{H}$-4'), 4.27–4.37 (m, 2, $\underline{H}$-2', $\underline{H}$-3'); 5.10 (t, 1, 5'-O$\underline{H}$, J=5 Hz), 5.18 (d, 1, 3'-O$\underline{H}$, J=4 Hz), 5.91 (d, 1, $\underline{H}$-1', J=6.6 Hz), 8.31 (s, 1, 8-$\underline{H}$), 11.73 (s, 1, C₂ amide) and 12.11 (s, 1, N₁ amide). Anal. Calcd. for C₂₃H₃₇N₅O₆: C, 57.60; H, 7.78; N, 14.60. Found: C, 57.63; H, 7.92; N, 14.62.

EXAMPLE 15

N2-Isobutyryl-5'-dimethoxytrityl-2'-O-nonylguanosine

N2-Isobutyryl-2'-O-nonylguanosine (14.6 g, 30.4 mmol) was treated with dimethoxytrityl chloride (12.1 g, 34 mmol) in pyridine (200 ml) as per the procedure of Example 5 to yield 16 g of purple foam prior to chromatography and 11.5 g after chromatography purification. ¹H NMR (DMSO-$\underline{d}_6$) δ 0.84 [t, 3, C$\underline{H}_3$(nonyl), J=7 Hz], 1.16 [m, 18, O—CH₂CH₂(C$\underline{H}_2$)₆, CH(CH₃)₂], 1.43 [m, 2, O—CH₂C$\underline{H}_2$(CH₂)₆], 2.77 [m, 1, C$\underline{H}$(CH₃)₂], 3.18–3.63 (m, 4, $\underline{H}$-5', O—C$\underline{H}_2$(CH₂)₇]; 3.74 (s, 6, DMTr O—C$\underline{H}_3$) 4.06 (m, 1, H-4'), 4.27 (m, 1, $\underline{H}$-3'); 4.42 (m, 1, $\underline{H}$- 2'); 5.19 (d, 1, 3'-O$\underline{H}$, J=5 Hz), 5.94 (d, 1, $\underline{H}$-1', J=5.7 Hz), 6.83–7.38 (m, 13, DMTr aromatic), 8.14 (s, 1, 8-$\underline{H}$), 11.65 (s, 1, C₂ amide) and 12.11 (s, 1, N₁ amide). Anal. Calcd. for C₄₄H₅₅N₅O₈: C, 67.59; H, 7.27; N, 8.96. Found: C, 67.59; H, 7.11; N, 8.80.

EXAMPLE 16

N2-Isobutyryl-5'-dimethoxytrityl-2'-O-nonylguanosine 3'-β-cyanoethyl-N,N-diisopropylphosphoramidate N2-Isobutyryl-5'-dimethoxytrityl-2'-O-nonylguanosine (2.1 g) was treated with bis-(N,N-diisopropylamino)-2-cyanoethyl-phosphine (1.5 g) and N,N-diisopropylammonium tetrazolide (0.2 g) as per the procedure of Example 6 to yield the product (2.0 g). ³¹P NMR (CDCl₂) δ 150.7 and 150.4 (diastereomers).

EXAMPLE 17

2,6-Diamino-9-(2,3-di-O-propyl-β-D-ribofuranosyl]purine

The procedure of Example 2 was repeated utilizing 2,6-diamino-9-(β-D-ribofuranosyl)purine (10 g), NaH (3 g) and 1-bromo-propane (10 ml) in DMF. After evaporation of the reaction solvent, the reaction products were purified by silica gel chromatography. The slower moving component yielded 4.3 g of the 2'-O-propyl product as a foam. This foam was crystallized from water to yield 3.6 g of product. The faster moving component isolated as an oil formed crystals upon standing. EtOH was added to the crystals, they were filtered and wash 1×EtOH to yield 1.1 grams of 2',3'-di-O-propyl product. m.p. 165°–167° C. $^1$H NMR (DMSO-$d_6$) δ 0.80 and 0.92 (t, 6, C$\underline{H}_3$), 1.6 and 1.45 (m, 4, C$\underline{H}_2$), 3.7–3.45 (br m, 6), 4.07 (m, 2), 4.5 (dd, 1), 5.55 (br t, 1, 5'-O$\underline{H}$), 5.8 (br s, 2, 6-N$\underline{H}_2$), 5.85 (d, 1, $\underline{H}$-1'), 6.84 (br s, 2, 2 -N$\underline{H}_2$) and 8.0 (s, 1, $\underline{H}$-8). Anal. Calcd. for $C_{16}H_{26}N_6O_4$: C, 52.45; H, 7.15; N, 22.94. Found: C, 52.18; H, 7.19; N, 22.75.

EXAMPLE 18

N2,N6-Diisobutyryl-2,6-diamino-9-(2-O-propyl-β-D-ribofuranosyl)purine 2,6-diamino-9-(2-O-propyl-β-D-ribofuranosyl)purine (2.0 g) in pyridine (35 ml) was treated with trimethylsilyl chloride (3.9 ml, 5 eq) and isobutyryl chloride (3.2 ml, 5 eq) as per the procedure of Example 4 to yield a foam after silica gel chromatography. The foam was crystallized from EtOAc/Hex to yield 2.2 g of product. m.p. 140°–142° C. $^1$H NMR (DMSO-$d_6$) δ 0.77 (t, 3, C$\underline{H}_3$), 1.07, 1.16 [d, 12, 2×CH(C$\underline{H}_3$)$_2$], 1.5 (m, 2, C$\underline{H}_2$), 2.9, 3.03 [m, 2, 2×C$\underline{H}$(CH$_3$)$_2$], 3.4 (m, 1, $\underline{H}$-5''), 3.58 (m, 3, OC$\underline{H}_2$, $\underline{H}$-5'), 3.95 (m, 1, $\underline{H}$-4'), 4.3 (m, 1), 4.5 (m, 1), 5.02 (t, 1, 5'-O$\underline{H}$), 5.2 (d, 1, 3'-O$\underline{H}$), 6.03 (d, 1, $\underline{H}$-1'), 8.58 (s, 1, $\underline{H}$-8), 10.39 (br s, 1, N$\underline{H}$), and 10.57 (br s, 1, N$\underline{H}$).

EXAMPLE 19

N2,N6-Diisobutyryl-2,6-diamino-9-(5-O-dimethoxytrityl-2-O-propyl-β-D-ribofuranosyl)purine N2,N6-Diisobutyryl-2,6-diamino-9-(2-O-propyl-β-D-ribo-furanosyl)purine (1.9 g) was treated with dimethoxytrityl chloride (1.5 g, 1.1 eq), and dimethylaminopyridine (20 mg as a catalyst) in pyridine (50 ml) as per the procedure of Example 5 to yield the product as a foam (2.8 g). $^1$H NMR (DMSO-$d_6$) δ 0.79 (t, 3, C$\underline{H}_3$), 1.07, 1.16 [d, 12, 2×CH(C$\underline{H}_3$)$_2$], 1.5 (m, 2, C$\underline{H}_2$), 2.9, 3.03 [m, 2, 2×C$\underline{H}$(CH$_3$)$_2$], 3.58 (m, 3, OC$\underline{H}_2$, $\underline{H}$-5'), 4.15 (m, 1, $\underline{H}$-4'), 4.4 (m, 1), 4.6 (m, 1), 5.15 (d, 1, 3'-O$\underline{H}$), 6.15 (d, 1, $\underline{H}$-1'), 6.8–7.35 (m, 13, DMTr), 8.5 (s, 1, $\underline{H}$-8), 10.3 (br s, 1, N$\underline{H}$), and 10.57 (br s, 1, N$\underline{H}$).

EXAMPLE 20

N2,N6-Diisobutyryl-2,6-diamino-9-(5-O-dimethoxytrityl-2-O-propyl-β-D-ribofuranosyl)purine 3'-β-cyanoethyl-N,N-diisopropylphosphoramidate N2,N6-Diisobutyryl-2,6-diamino-9-(5-O-dimethoxytrityl-2-O-propyl-β-D-ribofuranosyl)purine (2.6 g) was treated with bis-(N,N-diisopropylamino)-2-cyanoethylphosphite (1.7 g) and N,N-diisopropylammonium tetrazolide (300 mg) overnight at room temperature. The reaction mixture was partitioned against dil. Na$_2$CO$_3$/CHCl$_2$ and then Na$_2$CO$_3$/NaCl and dried over MgSO$_4$. The organic layer was evaporated to a foam. The foam was dissolved in CH$_2$Cl$_2$ (≈8 ml) and slowly added to Hexanes (500 ml). The solid was filtered and dried to yield the product as a powder (3.1 g). $^{31}$P NMR (CDCl$_3$) δ 150.8 and 151.3.

EXAMPLE 21

2,6-Diamino-9-[2-O-(N-phthalimido)propyl-β-D-ribofuranosyl]purine & 2,6-Diamino-9-[3-O-(N-phthalimido)propyl-β-D-ribofuranosyl]purine 2,6-Diamino-9-(β-D-ribofuranosyl)purine (14.2 g) was treated with sodium hydride (3 g, 1.5 eq) and N-(3-bromopropyl) phthalimide (5.3 ml, 1.5 eq) in DMF (20 g) at 70° C. overnight. The reaction mixture was proportioned between H$_2$O and Hexanes (1×), then extracted 4×CH$_2$Cl$_2$. The organic layer was dried over MgSO$_4$ and evaporated to a residue. The residue was purified by silica gel chromatography eluted with MeOH/CH$_2$Cl$_2$. The 2'-O-(N-phthalimido)propyl product eluted first followed by mixed fractions and then the 3'-O-(N-phthalimido) product. Evaporations of the fractions gave 3.4 g of the 2'-O-(N-phthalimido)propyl product, 3.0 g of mixed 2' and 3' products and 1.4 g of the 3'-O-(N-phthalimido)propyl product all as foams. The 3'-O-(N-phthalimido)propyl product was crystallized from EtOAc/MeOH to give 270 mg of solid.

2,6-Diamino-9-[2-O-(N-phthalimido)propyl-β-D-ribofuranosyl]purine $^1$H NMR (DMSO-$d_6$) δ 1.8 (tq, 2, —C$\underline{H}_2$—), 3.4–3.58 (m, 6, 2 ×C$\underline{H}_2$, $\underline{H}$-5'), 3.9 (m, 1), 4.26 (m, 1), 4.37 (m, 1), 5.05 (br d, 1, 3'-O$\underline{H}$), 5.4 (br t, 1, 5'-O$\underline{H}$), 5.72 (br s, 2, N$\underline{H}_2$), 5.8 (br d, 1, $\underline{H}$-1'), 6.75 (br s, 2, N$\underline{H}_2$), 7.8 (br s, 4, Ar) and 8.93 (s, 1, $\underline{H}$-8).

2,6-Diamino-9-[3-O-(N-phthalimido)propyl-β-D-ribofuranosyl]purine m.p. 220°–222° C., $^1$H NMR (DMSO-$d_6$) δ 1.85 (tq, 2, —C$\underline{H}$—N), 3.6–3.67 (m, 4, —O—C$\underline{H}_2$, $\underline{H}$-5'), 3.85 (m, 1), 3.92 (m, 1), 4.6 (m, 1), 5.33 (d, 1, 2'-O$\underline{H}$), 5.45 (br t, 1, 5'-O$\underline{H}$), 5.65 (d, 1, $\underline{H}$-1'), 5.73 (br s, 2, N$\underline{H}_2$), 6.75 (br d, 2, N$\underline{H}_2$), 7.8–7.85 (m, 4, Ar) and 7.85 (s, 1, $\underline{H}$-8). Anal. Calcd. for $C_{21}H_{23}N_7O_6$: C, 53.73; H, 4.94; N, 20.88. Found: C, 53.59; H, 4.89; N, 20.63.

EXAMPLE 22

2'-O-(N-Phthalimido)propylguanosine 2,6-diamino-9-[2-O-(N-phthalimido)propyl-β-D-ribofuranosyl] purine (3.1 g) in 0.1M sodium phosphate buffer (3 ml, pH 7.4), 0.05M tris buffer (65 ml, pH 7.4) and DMSO (45 ml) was treated with adenosine deaminase (200 mg) at room temperature for 5 days as per the procedure of Example 3. The product containing fractions from the silica gel chromatography were evaporated and upon concentration formed white crystals. The crystals were filtered and washed with MeOH to yield 1.1 g of product. An analytical sample was recrystallized from MeOH. m.p. 192°–194° C. $^1$H NMR (DMSO-$d_6$) δ 1.82 (m, 2, C$\underline{H}_2$), 3.45–3.67 (m, 6, $\underline{H}$-5', OC$\underline{H}_2$, NC$\underline{H}_2$ ), 3.9 (m, 1), 4.3 (m, 2, $\underline{H}$-2', $\underline{H}$-3'), 5.1 (m, 2, 5' and 3'-O$\underline{H}$ ), 5.8 (d, 1, $\underline{H}$-1'), 6.5 (br s, 2, N$\underline{H}_2$), 7.83 (s, 4, phthal), 7.98 (s, 1, $\underline{H}$-8) and 10.5 (br s, 1, N$\underline{H}$). Anal. Calcd. for $C_{21}H_{22}N_6O_7$·½H$_2$O: C, 52.61; H, 4.83; N, 17.53. Found: C, 52.52; H, 4.78; N, 17.38.

EXAMPLE 23

N2-Isobutyryl-2'-O-(N-phthalimido)propylguanosine

2'-O-(N-phthalimido)propylguanosine (7.2 g, crude) in pyridine (35 ml) was treated with trimethylsilyl chloride (11.6 ml, 5 eq) and isobutyryl chloride (8 ml, 5 eq) as per the procedure of Example 4 to yield the product as a crude foam ( 6.5 g). An analytical sample was obtained by crystallization from EtOAc. m.p. 166°–168° C. $^1$H NMR (DMSO-$d_6$) δ 1.15 [d, 6, —CH(C$\underline{H}_3$)$_2$e], 1.85 (m, 2, C$\underline{H}_2$ ), 2.8 [m, 1, C$\underline{H}$(CH$_3$)$_2$], 3.45–3.7 (m, 6, H-5', OC$\underline{H}_2$, NC$\underline{H}_2$ ), 3.95 (m, 1), 4.34 (m, 1), 4.4 (m, 1), 5.12 (t, 1, 5'-O$\underline{H}$), 5.18 (d, 1, 3'-O$\underline{H}$), 5.9 (d, 1, $\underline{H}$-1'), 7.83 (s, 4, phthal), 8.3 (s, 1, $\underline{H}$-8), 11.65 (br s, 1, N$\underline{H}$) and 12.1 (br s, 1, N$\underline{H}$). Anal. Calcd. for $C_{25}H_{28}N_6O_8 \cdot \frac{1}{2}H_2O$: C, 54.64; H, 5.32; N, 15.29. Found: C, 54.46; H, 5.39; N, 14.98.

EXAMPLE 24

N2-Isobutyryl-5'-dimethoxytrityl-2'-O-(N-phthalimido)propylguanosine

N2-Isobutyryl-2'-O-(N-phthalimido)propylguanosine (1.2 g) was treated with dimethoxytrityl chloride (820 mg, 1.1 eq), and dimethylaminopyridine (20 mg as a catalyst) in pyridine (50 ml) as per the procedure of Example 5 utilizing 1:1 Hex/EtOAc, then EtOAc then 5% MeOH/EtOAc with 1% TEA as eluent. The product containing fraction were evaporated to yield the product as a foam (1.7 g). $^1$H NMR (DMSO-$d_6$) δ 1.1 [d, 6, —CH(C$\underline{H}_3$)$_2$], 1.85 (m, 2, C$\underline{H}_2$) , 2.75 [m, 1, C$\underline{H}$ (CH$_3$)$_2$], 3.45–3.7 (m, 6, H-5', OC$\underline{H}_2$, NC $\underline{H}_2$), 3.75 (s, 6, OC$\underline{H}_3$), 4.0 (m, 1), 4.32 (m, 1), 4.4 (m, 1), 5.2 (d, 1, 3'-O$\underline{H}$), 5.93 (d, 1, $\underline{H}$-1'), 6.83, 7.2, 7.35 (m, 13, DMTr), 7.78 (s, 4, phthal), 8.15 (s, 1, $\underline{H}$-8), 11.6 (br s, 1, N$\underline{H}$) and 12.05 (br s, 1, N$\underline{H}$). Anal. Calcd. for $C_{46}H_{46}N_6O_{10} \cdot H_2O$: C, 64.18; H, 5.62; N, 9.76. Found: C, 64.42; H, 5.78; N, 9.53.

EXAMPLE 25

N2-Isobutyryl-5'-dimethoxytrityl-2'-O-(N-phthalimido)propylguanosine 3'-β-cyanoethyl-N,N-diisopropylphosphoramidate N2-Isobutyryl-5'-dimethoxytrityl-2'-O-(N-phthalimido) propylguanosine (1.6 g) was treated with bis-(N,N-diisopropylamino)-2-cyanoethylphosphite (1.48 g) and N,N-diisopropylammoniumtetrazolide (200 mg) as per the procedure of Example 6 to yield the product (2.0 g). $^{31}$P NMR (CDCl$_3$) δ 150.9.

EXAMPLE 26

N2-Dimethylaminomethylidene-5'-dimethoxytrityl-2'-O-(N-phthalimido)propylguanosine 2'-O-(N-phthalimido)propylguanosine (900 mg) in DMF (20 ml) was treated with N,N-dimethylformamide dimethyl acetal (2 ml). The reaction mixture was stirred for 2 hr and evaporated under high vac at 52° C. The residue was co-evaporated 1×with pyridine and taken up in solution in pyridine. Dimethoxytrityl chloride (713 mg, 1.1 eq) and dimethylaminopyridine (20 mg as a catalyst) were added. The reaction mixture was stirred overnight, partitioned between Na$_2$CO$_3$/CH$_2$Cl$_2$, dried over MgSO$_4$ and purified by silica gel chromatography as per the procedure of Example 5 to yield 1.7 g of product as an off white solid. $^1$H NMR (DMSO-$d_6$) δ 1.88 (m, 2, C$\underline{H}_2$), 3.1 [d, 6, N=CHN(C$\underline{H}_3$)$_2$], 3.3 (m, 2, $\underline{H}$ -5'), 3.67 (m, 4, OC$\underline{H}_2$, NC$_2$), 3.78 (s, 6, 2×OC$\underline{H}_3$), 4.0 (m, 1, $\underline{H}$ -4'), 4.35 (m, 2, $\underline{H}$-2', $\underline{H}$-3'), 5.2 (d, 1, 3'-O$\underline{H}$), 5.95 (d, 1, $\underline{H}$-1'), 6.85, 7.25, 7.39 (m, 13, DMTr), 7.85 (s, 4, phthal), 7.95 [s, 1, $\underline{H}$-8), 8.5 (s, 1, N=C $\underline{H}$N(CH$_3$)$_2$] and 11.39 (s, 1, N$\underline{H}_2$). Anal. Calcd. for $C_{45}H_{45}N_7O_9 \cdot \frac{1}{2}H_2O$: C, 64.58; H, 5.54; N, 11.71. Found: C, 64.10; H, 5.65; N, 11.47.

EXAMPLE 27

N2-Dimethylaminomethylidene-5'-dimethoxytrityl-2'-O-(N-phthalimido)propylguanosine 3'-β-cyanoethyl-N,N-diisopropylphosphoramidate N2-Isobutyryl-5'-dimethoxytrityl-2'-O-(N-phthalimido) propylguanosine (1.7 g), bis-(N,N-diisopropylamino)-2-cyanoethylphosphite (1.4 ml) and N,N-diisopropylammonium tetrazolide (170 mg) were stirred overnight at room temperature. The reaction mixture was partitioned between CH$_2$Cl$_2$ and Na$_2$CO$_3$ 2 ×. The organic phase was dried over MgSO$_4$ and evaporated to an oil. The oil was dissolved in a minimum of CH$_2$Cl$_2$ and added dropwise to ≈900 ml Hexanes to precipitate the product. The solid was isolated and dried to yield 2.1 g of product. $^1$P NMR (CDCl$_3$) δ 150.4, 150.6.

EXAMPLE 28

2,6-Diamino-9-[2-O-(N-phthalimido)pentyl-β-D-ribofuranosyl] purine 2,6-Diamino-(9-β-D-ribofuranosyl)purine (6.7 g) was treated with sodium hydride (1.3 g) and N-(3-bromopentyl) phthalimide (7.8 g, 1.1 eq) in DMF (60 ml) at room temperature for three days. The reaction mixture was proportioned between H$_2$O and CH$_2$Cl$_2$ and extracted 4×CH$_2$Cl$_2$. The combined organic layers were dried over MgSO$_4$ and evaporated to a residue. The residue was purified by silica gel chromatography eluted with 5→10% MeOH/CH$_2$Cl$_2$. The 2'-O-(N-phthalimido)pentyl containing fractions were collected and evaporated to a yellow foam to give 2.2 g of product. An analytical sample was crystallized from EtOH. m.p. 173°–175° C. $^1$H NMR (DMSO-$d_6$) δ 1.2 (m, 2, —C$\underline{H}_2$—), 1.47 (m, 4, 2×C$\underline{H}_2$), 3.55, 3.65 (m, 6, O—C$\underline{H}_2$, $\underline{H}$-5', NC$\underline{H}_2$), 3.95 (m, 1), 4.28 (m, 1), 4.4 (m, 1), 5.13 (d, 1, 3'-O$\underline{H}$), 5.5 (t, 1, 5'-O$\underline{H}$), 5.77 (br s, 2, 6-N$\underline{H}_2$), 5.84 (br d, 1, $\underline{H}$-1'), 6.8 (br s, 2, 2-N$\underline{H}_2$), 7.86 (M, 4, phthal) and 7.95 (s, 1, $\underline{H}$-8). Anal. Calcd. for $C_{23}H_{27}N_7O_6$: C, 55.50; H, 5.47; N, 19.71. Found: C, 55.44; H, 5.51; N, 19.30.

EXAMPLE 29

2'-O-(N-Phthalimido)pentylguanosine

A mixture of the 2,6-diamino-9-[2-O-(N-phthalimido) pentyl-β-D-ribofuranosyl]purine and 2,6-diamino-9-[3-O-(N-phthalimido) pentyl-β-D-ribofuranosyl]purine isomers (2.2 g) in 0.1M tris buffer (60 ml, pH 7.4), 0.1M NaPO$_4$ buffer (2 ml, pH 7.4) and DMSO (40 ml) was treated with adenosine deaminase (60 mg) at room temperature for 5 days as the procedure of Example 3. The product containing fractions from the silica gel chromatography were evaporated to give the product (1.0 g) as a crude white solid. An analytical sample was prepared by the addition of MeOH to form crystals. m.p. 178°–180° C. $^1$H NMR (DMSO-$d_6$) δ 1.24 (m, 2, C$\underline{H}_2$), 1.5 (m, 4, 2×C$\underline{H}_2$), 3.5–3.6 (m, 6, $\underline{H}$-5', OC$\underline{H}_2$, NC$\underline{H}_2$ ), 3.87 (m, 1, $\underline{H}$-4'), 4.25 (m, 2, $\underline{H}$-2', $\underline{H}$-3'), 5.1 (m, 2, 5' and 3 '-O$\underline{H}$), 5.78 (d, 1, $\underline{H}$-1'), 6.5

(br s, 2, N$\underline{H}_2$), 7.84 (M, 4, phthal), 7.98 (s, 1, $\underline{H}$-8) and 10.67 (br s, 1, N$\underline{H}$). Anal. Calcd. for $C_{23}H_{26}N_6O_7 \cdot \frac{1}{2} H_2O$: C, 54.43; H, 5.36; N, 16.56. Found: C, 54.79; H, 5.24; N, 16.61.

EXAMPLE 30

N2-Isobutyryl-2'-O-(N-phthalimido)pentylguanosine

2'-O-(N-phthalimido)pentylguanosine (1.6 g, crude) in pyridine (35 ml) was treated with trimethylsilyl chloride (2.0 ml, 5 eq) and isobutyryl chloride (1.68 ml, 5 eq) as per the procedure of Example 4 to yield the product as a foam. This foam was co-evaporated 2×with EtOAc followed by the addition of EtOAc and heating to yield white crystals (950 mg). m.p. 202°–204° C. $^1$H NMR (DMSO-$\underline{d}_6$) δ 1.1 [d, 6, —CH(C$\underline{H}_3$)$_2$], 1.17 (m, 2, C$\underline{H}_2$), 1.43 (m, 4, 2×C$\underline{H}_2$), 2.74 [m, 1, C$\underline{H}$(CH$_3$)$_2$], 3.45–3.55 (m, 6, H-5', OC$\underline{H}_2$, NC$\underline{H}_2$), 3.9 (m, 1), 4.25 (m, 1), 4.3 (m, 1), 5.07 (t, 1, 5'-O$\underline{H}$), 5.15 (d, 1, 3'-O$\underline{H}$), 5.87 (d, 1, $\underline{H}$-1'), 7.8 (s, 4, phthal), 8.27 (s, 1, $\underline{H}$-8), 11.67 (br s, 1, N$\underline{H}$) and 12.06 (br s, 1, N$\underline{H}$). Anal. Calcd. for $C_{27}H_{32}N_6O_8 \cdot \frac{1}{2}H_2O$: C, 56.14; H, 5.76; N, 14.55. Found: C, 56.45; H, 5.74; N, 14.41.

EXAMPLE 31

N2-Isobutyryl-5'-dimethoxytrityl-2'-O-(N-phthalimido)pentylguanosine

N2-Isobutyryl-2'-O-(N-phthalimido)pentylguanosine (0.95 g) was treated with dimethoxytrityl chloride (620 mg, 1.1 eq), and dimethylaminopyridine (20 mg as a catalyst) in pyridine (50 ml) as per the procedure of Example 5 utilizing EtOAc 1% TEA and then 5% MeOH EtOAc/CH$_2$Cl$_2$ with 1% TEA as eluent. The product containing fractions were evaporated to yield the product as a foam (1.4 g). $^1$H NMR (DMSO-$\underline{d}_6$) δ 1.14 [d, 6, —CH(C$\underline{H}_3$)$_2$], 1.25 (m, 2, C$\underline{H}_2$), 1.53 (m, 4, 2 ×C$\underline{H}_2$), 2.77 [m, 1, C$\underline{H}$(CH$_3$)$_2$], 3.3–3.6 (m, 6, H-5', OC$\underline{H}_2$, NC$\underline{H}_2$), 3.75 (s, 6, OC$\underline{H}_3$), 4.07 (m, 1), 4.33 (m, 1), 4.4 (m, 1), 5.18 (d, 1, 3'-O$\underline{H}$), 5.94 (d, 1, $\underline{H}$-1'), 6.83, 7.2, 7.53 (m, 13, DMTr), 7.8 (s, 4, phthal), 8.15 (s, 1, $\underline{H}$-8), 11.6 (br s, 1, N$\underline{H}$) and 12.1 (br s, 1, N$\underline{H}$). Anal. Calcd. for $C_{48}H_{50}N_6O_{10} \cdot \frac{1}{2}H_2O$: C, 65.52; H, 5.84; N, 9.55. Found: C, 65.55; H, 5.94; N, 9.20.

EXAMPLE 32

2,6-Diamino-9-[3,5-O-(tetraisopropyldisiloxane-1,3-diyl)-β-D-ribofuranosyl]purine To a suspension of 2,6-diamino-9-(β-D-ribofuranosyl)purine (10.5 g) in pyridine (100 ml) was added 1,3-dichlorotetraisopropyldisiloxane (TIPDS, 12.6 g). The reaction was stirred at room temperature for 4 hours and an additional 1.3 g of 1,3-dichlorotetraisopropyldisiloxane was added followed by stirring overnight. The reaction mixture was poured into ice water and the insoluble product (11.6 g) collected by filtration. An analytical sample was recrystallized from EtOAc/Hexanes. m.p. 170°–172° C. Anal. Calcd. for $C_{22}H_{40}N_6O_5Si_2 \cdot \frac{1}{2}H_2O$: C, 49.5; H, 7.74; N, 15.7. Found: 49.57; H, 7.82; N, 15.59.

EXAMPLE 33

2,6-Diamino-9-[3,5-O-(tetraisopropyldisiloxane-1,3-diyl)-2-O-methyl-β-D-ribofuranosyl]purine A mixture of 2,6-Diamino-9-[3,5-O-(tetraisopropyldisiloxane-1,3-diyl)-β-D-ribofuranosyl]purine (8.8 g) in DMF (120 ml) and methyl iodide (3 ml, 3 eq) was cooled in an ice bath and NaH (60% in oil, 1.0 g, 1.5 eq) added. After 20 min the reaction was quenched with MeOH and partitioned between sat. NH$_4$Cl and CH$_2$Cl$_2$. The organic phase was washed with 1×NH$_4$Cl, dried over MgSO$_4$ and evaporated. The residue was crystallized from hot EtOH/H$_2$O to yield the product (8.5 g) as crystals. m.p. 87°–89° C. $^1$H NMR (DMSO-$\underline{d}_6$) δ 1.05 (m, 28, TIPDS), 3.57 (s, 3, OC$\underline{H}_3$), 3.98 (m, 1, $\underline{H}$-4'), 3.92 and 4.07 (ABX, 2, $\underline{H}$-5'), 4.13 (d, 1), 4.6 (dd, 1, $\underline{H}$-3'), 5.76 (br s, 2, N$\underline{H}_2$), 5.8 (s, 1, $\underline{H}$-1'), 6.77 (br s, 2, N$\underline{H}_2$) AND 7.77 (s, 1 $\underline{H}$-8).

EXAMPLE 34

2,6-Diamino-9-(2-O-methyl-β-D-ribofuranosyl)purine

To a solution of 2,6-Diamino-9-[3,5-O-(tetraisopropyldisiloxane-1,3-diyl)- 2-O-methyl-S-D-ribofuranosyl]purine (8.5 g) in THF (50 ml) was added 1M tetrabutylammonium fluoride in THF (Aldrich, 20 ml). The reaction mixture was stirred for 2 hrs and filtered. The filter cake was washed with 2×EtOAc and air dried to give 4.0 g of crude product. An analytical sample was crystallized from hot MeOH. m.p. 133°–135° C. $^1$H NMR (DMSO-$\underline{d}_6$) δ 3.3 (s, 3, OC$\underline{H}_3$), 3.58 (m, 2, $\underline{H}$-5'), 3.98 (m, 1, $\underline{H}$-4'), 4.28 (m, 2, $\underline{H}$-2 ', $\underline{H}$-3'), 5.23 (br s, 1, 3'-O$\underline{H}$), 5.48 (br t, 1, 5'-O$\underline{H}$), 5.77 (br s, 2, N$\underline{H}_2$), 5.82 (d, 1, $\underline{H}$-1'), 6.83 (br s, 2, N$\underline{H}_2$) and 7.95 (s, 1, $\underline{H}$-8). Anal. Calcd. for $C_{11}H_{16}N_6O_4 \cdot \frac{1}{2}H_2O$: C, 43.28; H, 5.61; N, 27.52. Found: C, 43.51; H, 5.62; N, 27.26.

EXAMPLE 35

2'-O-Methylguanosine 2,6-Diamino-9-(2-O-methyl-β-D-ribofuranosyl)purine (9.5 g) in 0.1M sodium phosphate buffer (200 ml, pH 7.4) and DMSO (25 ml) was treated with adenosine deaminase (Type II Sigma) at RT for 4 days. The resulting suspension was cooled and filtered and the resulting filter cake washed with H$_2$O and dried to a white solid (4.0 g). The solid was recrystallized from hot H$_2$O to yield 2.9 g of product. m.p. 236°–238° C. $^1$H NMR (DMSO-$\underline{d}_6$) δ 3.3 (s, 3, OC$\underline{H}_3$), 3.53 and 3.6 (ABX, 2, $\underline{H}$-5'), 3.87 (m, 1, $\underline{H}$-4'), 4.15 (m, 1, $\underline{H}$-2'), 4.25 (m, 1, $\underline{H}$-3'), 5.13 (t, 1, 5'-O$\underline{H}$), 5.23 (d, 1, 3'-O$\underline{H}$), 5.8 (d, 1, $\underline{H}$-1'), 6.48 (br s, 2, N$\underline{H}_2$), 7.96 (s, 1, $\underline{H}$-8) and 10.68 (br s, 1, N$\underline{H}$). Anal. Calcd. for $C_{11}H_{15}N_5O_5 \cdot \frac{1}{2}H_2O$: C, 43.14; H, 5.26; N, 22.86. Found: C, 43.59; H, 5.34; N, 23.04.

EXAMPLE 36

N2-Isobutyryl-2'-O-methylguanosine

2'-O-methylguanosine (3.5 g) in pyridine (100 ml) was treated with trimethylsilyl chloride (9 ml, 6 eq) and isobutyryl chloride (6.2 ml) at RT for 4 hr. The reaction mixture was cooled in an ice bath, H$_2$O (20) was added and stirring continued for an additional 20 min. NH$_4$OH (20 ml) was added and after stirring for 30 min the reaction mixture was evaporated. The residue was triturated with H$_2$O, filtered and the filtrate evaporated and purified by silica gel chromatography as per the procedure of Example 4 to yield the product as an off white solid (1.5 g). $^1$H NMR (DMSO-$\underline{d}_6$) δ 1.1 [d, 6, CH(C$\underline{H}_3$)$_2$], 2.77 [m, 1, C$\underline{H}$(CH$_3$)$_2$], 3.33–3.6 (m, 5, OC$\underline{H}_3$, $\underline{H}$-5'), 3.93 (m, 1, $\underline{H}$-4 '), 4.22 (m, 1), 4.3 (m, 1), 5.1 (t, 1, 5'-O$\underline{H}$), 5.28 (d, 1, 3'-O$\underline{H}$), 5.9 (d, 1, $\underline{H}$-1'), 8.28 (s, 1, $\underline{H}$-8) and 11.9 (br s, 1, N$\underline{H}$).

EXAMPLE 37

N2-Isobutyryl-5'-dimethoxytrityl-2'-O-methylguanosine

N2-Isobutyryl-2'-O-methylguanosine (1.5 g) was treated with dimethoxytrityl chloride (1.5 g, 1.1 eq), and dimethylaminopyridine (100 mg as a catalyst) in pyridine (50 ml) as per the procedure of Example 5 to yield the product as a foam (2.6 g). $^1$H NMR (DMSO-$d_6$) δ 1.14 (d, 6, CH(C$\underline{H}_3)_2$], 2.75 [m, 1, C$\underline{H}$(CH$_3)_2$], 3.5 (m, 2, $\underline{H}$-5'), 3.74 (s, 6, OC$\underline{H}_3$), 4.05 (m, 1), 4.33 (m, 1), 5.26 (d, 1, 3'-O$\underline{H}$), 5.95 (d, 1, $\underline{H}$-1'), 6.83, 7.2, 7.35 (m, 13, DMTr), 8.15 (s, 1, $\underline{H}$-8), 11.6 (br s, 1, N$\underline{H}$) and 12.1 (br s, 1, N$\underline{H}$).

EXAMPLE 38

N2-Isobutyryl-5'-dimethoxytrityl-2'-O-methylguanosine 3'-β-cyanoethyl-N,N-diisopropylphosphoramidate N2-Isobutyryl-5'-dimethoxytrityl-2'-O-methylguanosine (20 g) was treated with bis-(N,N-diisopropylamino)-2-cyanoethylphosphite (10.8 g) and N,N-diisopropylammonium tetrazolide (1.6 g) as per the procedure of Example 6 to yield the product (15.7 g). $^{31}$P NMR (CDCl$_3$) δ 148.97 and 147.96.

EXAMPLE 39

N2,N6-Diisobutyryl-2,6-diamino-9-(2-O-methyl-β-D-ribofuranosyl) purine 2,6-diamino-9-(2-O-methyl-β-D-ribofuranosyl)purine (700 mg) in pyridine (20 ml) was treated with trimethylsilyl chloride (2.1 ml, 7 eq) and isobutyryl chloride (1.25 ml, 5 eq) as per the procedure of Example 4 to yield the product as a foam (900 mg) after silica gel chromatography.

EXAMPLE 40

N2,N6-Diisobutyryl-2,6-diamino-9-(5-O-dimethoxytrityl-2-O-methyl-β-D-ribofuranosyl)purine N2,N6-Diisobutyryl-2,6-diamino-9-(2-O-methyl-β-D-ribofuranosyl)purine (900 mg) was treated with dimethoxytrityl chloride (1.0 g) and dimethylaminopyridine (20 mg as a catalyst) in pyridine (30 m) as per the procedure of Example 5 to yield the product as a foam (700 mg). $^1$H NMR (DMSO-$d_6$) δ 0.96–1.16 [m, 12, 2×CH(CH$_3)_2$], 2.9 and 3.05 [M, 2, 2×C$\underline{H}$(CH$_3)_2$], 3.18 and 3.37 (ABX, 2, $\underline{H}$-5'), 3.38 (s, 3, OC$\underline{H}_3$), 3.7 (s, 6, OC$\underline{H}_3$), 4.05 (m, 1, $\underline{H}$-4'), 4.44 (m, 2, $\underline{H}$-2',H-3'), 5.24 (d, 1, 3'-O$\underline{H}$), 6.06 (d, 1, $\underline{H}$-1'), 6.78, 7.2, 7.33 (m, 13, Ar), 8.22 (s, 1, $\underline{H}$-8), 10.3 (br s, 1, N$\underline{H}$) and 10.57 (br s, 1, N$\underline{H}$).

EXAMPLE 41

N2,N6-Diisobutyryl-2,6-diamino-9-(5-O-dimethoxytrityl-2-O-methyl-β-D-ribofuranosyl)purine 3'-β-cyanoethyl-N,N-diisopropylphosphoramidate N2,N6-Diisobutyryl-2,6-diamino-9-(5-O-dimethoxytrityl-2-O-methyl-β-D-ribofuranosyl)purine (600 mg) was treated with bis-(N,N-diisopropylamino)-2-cyanoethylphosphite (500 μl) and N,N-diisopropylammonium tetrazolide (80 mg) overnight at RT. The reaction mixture was partitioned against dil. Na$_2$CO$_3$/CHCl$_2$ and then Na$_2$CO$_3$/NaCl and dried over MgSO$_4$. The organic layer was evaporated to a foam (500 mg). $^{31}$P NMR (CDCl$_3$) δ 151.1 (doublet).

EXAMPLE 42

2,6-Diamino-9-(2-O-octadecyl-β-D-ribofuranosyl)purine 2,6-Diamino-9-(β-D-ribofuranosyl)purine (50 g, 180 mmol) and sodium hydride (7 g) in DMF (1 l) were heated to boiling for 2 hr. Iodooctadecane (100 g) was added at 150° C. and the reaction mixture allowed to cool to RT. The reaction mixture was stirred for 11 days at RT. The solvent was evaporated and the residue purified by silica gel chromatography. The product was eluted with 5% MeOH/CH$_2$Cl$_2$. The product containing fraction were evaporated to yield the product (11 g). $^1$H NMR (DMSO-$d_6$) δ 0.84 (t, 3, C$\underline{H}_2$); 1.22 [m, 32, O—CH$_2$—CH$_2$—(C$\underline{H}_2)_{16}$—]; 1.86 (m, 2, O—CH$_2$ C$\underline{H}_2$—); 3.25 (m, 2, O—C$\underline{H}_2$—); 3.93 (d, 1, 4' $\underline{H}$), 4.25 (m, 1, 3'$\underline{H}$); 4.38 (t, 1, 2'$\underline{H}$); 5.08 (d, 1, 3'-O$\underline{H}$); 5.48 (t, 1, 5'-O$\underline{H}$); 5.75 (s, 2, 6-N$\underline{H}_2$); 5.84 (d, 1, 1'-$\underline{H}$); 6.8 (s, 2, 2-N$\underline{H}_2$); and 7.95 (s, 1, 8-$\underline{H}$).

EXAMPLE 43

2'-O-Octadecylguanosine 2,6-Diamino-9-(2-O-octadecyl-β-D-ribofuranosyl) purine (10 g) in 0.1M sodium phosphate buffer (50 ml, pH 7.4), 0.1M tris buffer (1000 ml, pH 7.4) and DMSO (1000 ml) was treated with adenosine deaminase (1.5 g) as per the procedure of Example 3. At day 3, day 5 and day 7 an additional aliquot (500 mg, 880 mg and 200 mg, respectively) of adenosine deaminase was added. The reaction was stirred for a total of 9 day and after purification by silica gel chromatography yielded the product (2 g). An analytical sample was recrystallized from MeOH $^1$H NMR (DMSO-$d_6$) δ 0.84 (t, 3, C$\underline{H}_3$), 1.22 [s, 32, O—CH$_2$—CH$_2$—(C$\underline{H}$)$_{16}$], 5.07 (m, 2, 3'-O$\underline{H}$ 5'-O$\underline{H}$); 5.78 (d, 1, 1'-$\underline{H}$); 6.43 (s, 2, N$\underline{H}_2$), 7.97 (s, 1, 8-$\underline{H}$) and 10.64 (s, 1, N$\underline{H}_2$). Anal. Calcd. for C$_{28}$H$_{49}$N$_5$O$_5$: C, 62.80; H, 9.16; N, 12.95. Found: C, 62.54; H, 9.18; N, 12.95.

EXAMPLE 44

N2-Isobutyryl-2'-O-octadecylguanosine

2'-O-Octadecylguanosine (1.9 g) in pyridine (150 ml) was treated with trimethylsilyl chloride (2 g, 5 eq) and isobutyryl chloride (2 g, 5 eq) as per the procedure of Example 4. The product was purified by silica gel chromatography (eluted with 3% MeOH/EtOAc) to yield 1.2 g of product. $^1$H NMR (DMSO-$d_6$) δ 0.85 [t, 3, C$\underline{H}_3$], 1.15 [m, 38, O—CH$_2$CH$_2$(C$\underline{H}_2)_{16}$, CH(C$\underline{H}_3)_2$], 2.77 [m, 1, C$\underline{H}$(CH$_3)_2$], 4.25 (m, 2, 2' $\underline{H}$, 3'$\underline{H}$); 5.08 (t, 1, 5'-O$\underline{H}$), 5.12 (d, 1, 3'-O$\underline{H}$), 5.87 (d, 1, 1'-$\underline{H}$), 8.27 (s, 1, 8-$\underline{H}$), 11.68 (s, 1, N$\underline{H}_2$) and 12.08 (s, 1, N$\underline{H}_2$). Anal. Calcd. for C$_{32}$H$_{55}$N$_5$O$_6$: C, 63.47; H, 9.09; N, 11.57. Found: C, 63.53; H, 9.20; N, 11.52.

EXAMPLE 45

2,6-Diamino-9-[2-O-(imidazol-1-yl)butyl-β-D-ribofuranosyl] purine 2,6-Diamino-(9-β-D-ribofuranosyl)purine (5.0 g) in DMF (400 ml) was treated with sodium hydride (0.78 g). After stirring an additional 30 min a further portion of sodium hydride (2.6 g) was added immediately followed by bromobutylimidazole (9.9 g) in DMF (25 ml). The reaction mixture was stirred overnight and quenched with H$_2$O. The reaction mixture was filtered through celite and evaporated to yield an oily product. TLC showed a mixture of isomers.

EXAMPLE 46

2'-O-(Imidazol-1-yl)butylguanosine

A mixture of the 2,6-diamino-9-[2-O-(imidazol-1-yl)butyl-β-D-ribofuranosyl]purine and 2,6-diamino-9-[3-O-(imidazol-1-yl)butyl-β-D-ribofuranosyl]purine isomers in 0.1M tris buffer (pH 7.4), 0.1M NaSO$_4$ buffer (pH 7.4) and DMSO will treated with adenosine deaminase at RT for 5 days as per the procedure of Example 3. The product containing fractions will be purified by silica gel chromatography and the product containing fraction evaporated to give the product.

EXAMPLE 47

N2-Isobutyryl-2'-O-(imidazol-1-yl)butylguanosine

2'-O-(imidazol-1-yl)butylguanosine in pyridine will be treated with trimethylsilyl chloride (5 eq) and isobutyryl chloride (5 eq) as per the procedure of Example 4 to yield the product.

EXAMPLE 48

N2-Isobutyryl-5'-dimethoxytrityl-2'-O-(imidazol-1-yl)butylguanosine

N2-Isobutyryl-2'-O-(imidazol-1-yl)butylguanosine will be treated with dimethoxytrityl chloride (1.1 eq), and dimethylaminopyridine (as a catalyst) in pyridine as per the procedure of Example 5. After chromatography purification, the product containing fractions will be evaporated to yield the product).

What is claimed is:

1. A process for preparing 2'-O-substituted guanosine comprising the steps of:
    a) reacting 2,6-diaminopurine riboside with a base of sufficient strength to remove a proton from the 2'-hydroxyl or 3'-hydroxyl of 2,6-diaminopurine riboside, and with a compound having the formula R—L wherein R is an aliphatic or alicyclic group and L is a leaving group, to form 2'-O-substituted-2,6-diaminopurine riboside and 3'-O-substituted-2,6-diaminopurine riboside wherein said substituent is said aliphatic or alicylic group; and
    b) deaminating said 2'-O-substituted-2,6-diaminopurine riboside to yield said 2'-O-substituted guanosine; and
    c) recovering said 2'-O-substituted guanosine.

2. The process of claim 1 further comprising: separating said 2'-O-substituted-2,6-substituted diaminopurine riboside from said 3'-O-2,6-diaminopurine riboside.

3. The process of claim 1 wherein said 2'-O-substituted-2,6-diaminopurine riboside is deaminated with adenosine deaminase.

4. The process of claim 1 wherein said base is sodium hydride.

5. The process of claim 1 wherein said 2'-O-substituted-2,6-diaminopurine riboside is physically separated from said 3'-O-substituted-2,6-diaminopurine riboside by crystallization or chromatography.

6. A process for preparing 2'-O-substituted-2,6-diaminopurine riboside, 3'-O-substituted-2,6-diaminopurine riboside, and 2',3'-di-O-substituted-2,6-diaminopurine riboside comprising the steps of:
    a) reacting 2,6-diaminopurine riboside with a base of sufficient strength to remove a proton from the 2'- or 3'-hydroxyl of 2,6-diaminopurine riboside and with a compound having the formula R—L wherein R is an aliphatic or alicyclic group and L is a leaving group, to form at least one compound selected from the group consisting of 2'-O-substituted-2,6-diamino-purine riboside, 3'-O-substituted-2,6-diamino-purine riboside, and 2',3'-di-O-substituted-2,6-diaminopurine riboside wherein said substituent is an aliphatic or an alicyclic group; and
    b) isolating one of said substituted-2,6-diaminopurine ribosides.

7. The process of claim 6 further comprising adding sufficient compound R—L and base to form at least two of the compounds selected from the group consisting of 2'-O-substituted-2,6-diaminopurine riboside, 3'-O-substituted-2,6-diaminopurine riboside, and 2',3'-di-O-substituted-2,6-diaminopurine riboside; and separating out at least one of said substituted 2,6-diaminopurine riboside compounds.

8. The process of claim 7 further comprising separating out at least one specific substituted-2,6-diaminopurine riboside by crystallization.

9. The process of claim 7 further comprising separating out at least one specific substituted-2,6-diaminopurine riboside by chromatography.

10. The process of claim 1 wherein said aliphatic or alicyclic group is selected from the group consisting of $C_{1-20}$ straight chain alkyl, $C_{1-20}$ branched alkyl, $C_{1-20}$ straight chain alkenyl, $C_{1-20}$ branched chain alkenyl, $C_{1-20}$ straight chain alkynyl, and $C_{1-20}$ branched chain alkynyl.

11. The process of claim 10 wherein said aliphatic or alicyclic group bears a substituent selected from the group consisting of halogen, hydroxyl, thiol, keto, carboxyl, nitrate, nitro, nitroso, nitrile, trifluoromethyl, trifluoromethoxy, O-alkyl, S-alkyl, NH-alkyl, N-dialkyl, O-aralkyl, S-aralkyl, NH-aralkyl, amino, azido, hydrazino, hydroxylamino, isocyanato, sulfoxide, sulfone, sulfide, disulfide, silyl, heterocyclic, alicylic, intercalators, polyamines, polyamides, polyethylene glycols, and polyethers.

12. The process of claim 10 wherein said aliphatic or alicyclic group is substituted with a carbocylic group.

13. The process of claim 10 wherein said aliphatic or alicyclic group is substituted with a reporter molecule.

* * * * *

UNITED STATES PATENT AND TRADEMARK OFFICE
CERTIFICATE OF CORRECTION

PATENT NO. : 5,506,351
DATED : April 9, 1996
INVENTOR(S) : McGee

It is certified that error appears in the above-indentified patent and that said Letters Patent is hereby corrected as shown below:

Column 8, line 62, remove "in vacuo" and insert --*in vacuo*--

Column 8, line 64, remove "in vacuo" and insert --*in vacuo*--

Column 9, line 19, remove "in vacuo" and insert --*in vacuo*--

Column 9, line 42, remove "in vacuo" and insert --*in vacuo*--

Column 9, line 66, remove "in vacuo" and insert --*in vacuo*--

Column 11, line 1, remove "(m,4, OC$\underline{H}_2$, $\underline{H}$-5)" and insert --(m,4, OC$\underline{H}_2$, $\underline{H}$-5')--

Column 15, line 60, remove "1xwidth" and insert --1 x with--.

UNITED STATES PATENT AND TRADEMARK OFFICE
CERTIFICATE OF CORRECTION

PATENT NO. : 5,506,351
DATED : April 9, 1996
INVENTOR(S) : McGee

It is certified that error appears in the above-indentified patent and that said Letters Patent is hereby corrected as shown below:

Column 17, line 12 remove "2xwidth" and insert --2 x with--.

Column 17, line 58, remove "1/2H $_2$" and insert --1/2H$_2$--.

Column 18, line 1, remove "Nail" and insert --NaH--.

Signed and Sealed this

Twenty-fourth Day of December, 1996

*Attest:*

BRUCE LEHMAN

*Attesting Officer*  *Commissioner of Patents and Trademarks*